United States Patent [19]

Sackner

[11] Patent Number: 4,567,185

[45] Date of Patent: Jan. 28, 1986

[54] ENDORPHIN BLOCKAGE

[75] Inventor: Marvin A. Sackner, Miami Beach, Fla.

[73] Assignee: Key Pharmaceuticals, Inc., Miami Beach, Fla.

[21] Appl. No.: 537,182

[22] Filed: Sep. 29, 1983

Related U.S. Application Data

[63] Continuation-in-part of Ser. No. 494,228, May 13, 1983, abandoned, which is a continuation-in-part of Ser. No. 480,439, Mar. 30, 1983, abandoned.

[51] Int. Cl.⁴ ............................................. A61K 31/44
[52] U.S. Cl. .................................................... 514/282
[58] Field of Search ......................... 424/260; 514/282

[56] References Cited

U.S. PATENT DOCUMENTS 4,454,142  6/1984  Tuttle .................................. 424/260

OTHER PUBLICATIONS

Chem. Abst. 93-179633d, (1980), 95-126220b, (1981), ⊕ 97-66289k, (1982).

*Primary Examiner*—Stanley J. Friedman
*Attorney, Agent, or Firm*—Sybil Meloy

[57] ABSTRACT

A method of permitting restful sleep at high altitudes is disclosed involving administration to a patient susceptible to Cheyne-Stokes respiration of a pharmaceutically acceptable amount of an endorphin-blocking compound capable of blocking the action of endogenous endorphins, whereby sleep interruptions characteristic of Cheyne-Stokes respiration are alleviated. There is also disclosed a method of permitting a continuous flow of oxygen to the brain cells in a sleeping patient otherwise susceptible to repeated interruptions of breathing that would retard the necessary steady flow of oxygen to brain cells to maintain their viable condition, which comprises administration prior to retiring of a pharmaceutically acceptable amount of an endorphin-blocking compound capable of blocking the action of endogenous endorphins to substantially obviate sleep interruptions that otherwise would occur. In a different embodiment there is provided a method of retarding the advance of the symptoms of senility in a patient having a gross loss of effective sleep and an erosion of viable brain cells due to the periodic disruption of sleep including periods of total lack of breathing depriving the brain of a necessary minimum oxygen level to sustain healthy brain tissue, said periodic disruption taking place during periods of sleep due to periodic cessation of breathing, said method comprising administering to said patient a chemical agent that blocks periodic cessation of breathing to maintain the necessary minimum oxygen level to sustain healthy brain tissue during periods of sleep.

Also provided is a method of retarding the symptoms of aging caused by a decreased level of oxygen in the bloodstream in a geriatric patient which promotes excessive endorphin levels, by administering to a geriatric patient with diminished oxygen circulation in the bloodstream an endorphin blocker, whereby the normal level of endorphin is restored, thereby obviating the effects of the excess endorphin.

5 Claims, No Drawings

ENDORPHIN BLOCKAGE

CROSS-REFERENCE TO RELATED APPLICATION

This application is a continuation-in-part of my copending application Ser. No. 494,228 filed May 13, 1983, now abandoned, which is a continuation-in-part of my copending application Ser. No. 480,439, filed Mar. 30, 1983, now abandoned.

SUMMARY OF THE INVENTION

In a first aspect of the invention there is provided a method of permitting restful sleep at high altitudes which comprises administration to a patient susceptible to Cheyne-Stokes respiration at said high altitudes of a pharmaceutically acceptable amount of an endorphin-blocking compound, said endorphin-blocking compound capable of blocking the action of endogenous endorphins, whereby sleep interruptions characteristic of Cheyne-Stokes respiration are alleviated. As examples of said endorphin-blocking compound may be mentioned 1-N-allyl-14-hydroxynordihydromorphinone(naloxone) and, as a preferred embodiment for oral administration, 6-methylene-6-desoxy-N-cyclopropylmethyl-14-hydroxydihydronormorphone(nalmefene). Naltrexone((-)-17-(cyclopropylmethyl)-4,5α-epoxy-3,14-dihydroxymorphin-6-one) is also suitable.

In a second aspect of the invention there is provided a method of permitting a continuous flow of oxygen to the brain cells in a sleeping patient otherwise susceptible to repeated interruptions of breathing which would retard the necessary steady flow of oxygen to said brain cells to maintain their viable condition, which comprises administration to said patient prior to retiring of a pharmaceutically acceptable amount of an endorphin-blocking compound, said endorphin-blocking compound being capable of blocking the action of endogenous endorphins, whereby sleep interruptions that otherwise would occur are substantially obviated. As examples of said endorphin-blocking compound may be mentioned 1-N-allyl-14-hydroxynordihydromorphinone(naloxone) and, as a preferred embodiment for oral administration, 6-methylene-6-desoxy-N-cyclopropylmethyl-14-hydroxydihydronormorphone(nalmefene). Naltrexone is a third compound that is an effective endorphin-blocker and which is considered a preferred embodiment of the present invention.

In accordance with a third aspect of the present invention there is provided a method of retarding the advance of the symptoms of senility in a patient having a gross loss of effective sleep and an erosion of viable brain cells due to the periodic disruption of sleep, including periods of total lack of breathing, depriving the brain of a necessary minimum oxygen level to sustain healthy brain tissue, said periodic disruption taking place during periods of sleep due to periodic cessation of breathing, said method comprising administering to said patient a chemical agent that blocks said periodic cessation of breathing, whereby said necessary minimum oxygen level to sustain healthy brain tissue is maintained during periods of sleep. 1-N-allyl-14-hydroxynordihydromorphinone(naloxone) and 6-methylene-6-desoxy-N-cyclopropylmethyl-14-hydroxydihydronormorphone(nalmefene) are examples of chemical agents suitable for use in the present invention. Naltrexone is a third compound that is an effective endorphin-blocker and which is considered a preferred embodiment of the present invention.

In accordance with a preferred embodiment of this aspect of the invention, the method provides that 6-methylene-6-desoxy-N-cyclopropylmethyl-14-hydroxydihydronormorphone(nalmefene) is administered as an oral dosage unit form. To avoid waking a patient during his normal sleeping period of six to eight hours, a sustained release oral dosage unit form is particularly preferred so that there is provided the chemical agent, such as 6-methylene-6-desoxy-N-cyclopropylmethyl-14-hydroxydihydronormorphone, during an entire period of overnight sleep.

In a further embodiment of the present invention there is provided an oral sustained release dosage unit form which comprises a plurality of individual polymer coated granules suitable for distribution in a meal of an elderly patient, said plurality of granules capable of providing 6-methylene-6-desoxy-N-cyclopropylmethyl-14-hydroxydihydronormorphone or a pharmaceutically acceptable salt thereof to a patient to provide a sustained release of 6-methylene-6-desoxy-N-cyclopropylmethyl-14-hydroxydihydronormorphone over a prolonged period of time.

In aging, the normal lung degenerates such that changes at necropsy are similar to that observed in clinically symptomatic patients with emphysema. Although normally-aged subjects do not have symptoms of breathlessness as do patients with emphysema because the extent of the pathologic changes is relatively minor, these alterations cause slight but definite decreases in the oxygen content of the arterial blood compared to young normal subjects.

Also provided is a method of retarding the symptoms of aging which are due to a decreased level of oxygen in the bloodstream in a geriatric patient (due to minor degrees of emphysema related to aging) which promotes excessive endorphin levels, which comprises administering to said geriatric patient with diminished oxygen circulation in the bloodstream an endorphin blocker, whereby the normal level of endorphin is restored, thereby obviating the effects of the excess endorphin.

DETAILED DESCRIPTION OF THE INVENTION

Sleep disorders have long been recognized in the sense that patients who are unable to "get a good night's sleep" may be cranky or have other problems, which have often been regarded even within the general medical community as not as serious as they may in fact be. In recent years, a limited number of sleep centers have been established at medical institutions for the study of such disturbances. Sleep disorders, however, play a significant role in a variety of illnesses and particularly conditions of the elderly, which often only gradually occur so that their impact is not as great as, for example, a sudden infection. Observations of the sleep habits of the elderly indicates that there is a significant occurrence of sleep interruptions in patients who are either senile or showing tendencies toward senility. Chronic sleep disturbances in such generally elderly patients result in prolonged periods, often of up to thirty seconds duration, where the patient ceases breathing altogether. Such sleep interruptions often take place repeatedly during what is a "normal" overnight sleep period.

While 1-N-allyl-14-hydroxynordihydromorphinone, disclosed in British Patent Specification No. 939,287, is a preferred endorphin blocker, it is particularly contemplated that 6-methylene-6-desoxy-N-cyclopropylmethyl-14-hydroxydihydronormorphone be used as a preferred embodiment as an oral dosage unit form is better suited as an oral preparation. While 6-methylene-6-desoxy-N-cyclopropylmethyl-14-hydroxydihydronormorphone may be administered as the free compound, it is contemplated that the pharmaceutically acceptable salts thereof are to be used as well, and 6-methylene-6-desoxy-N-cyclopropylmethyl-14-hydroxydihydronormorphone hydrochloride is specifically contemplated as a preferred embodiment of the present invention. See Fishman, U.S. Pat. No. 3,814,768.

A daily dosage of from about 20 to about 100 mg per day is contemplated for 6-methylene-6-desoxy-N-cyclopropylmethyl-14-hydroxydihydronormorphone in the oral dosage unit form, and in a more preferred embodiment, it is specifically contemplated that a sustained release dosage form is provided to give at least about six to about eight hours release of 6-methylene-6-desoxy-N-cyclopropylmethyl-14-hydroxydihydronormorphone. With such an oral sustained release dosage unit form, the subject typically takes a single tablet, capsule, or granules just after dinner, so that the medication will be provided in the bloodstream throughout the period of overnight sleep.

Oral sustained release granules are used in a preferred embodiment for the oral sustained release dosage unit forms which contain a plurality of such granules. The oral sustained release dosage form is in one embodiment prepared from a plurality of such granules, each of which contains an essentially uniform distribution of 6-methylene-6-desoxy-N-cyclopropylmethyl-14-hydroxydihydronormorphone hydrochloride contained in a matrix to provide the uniform release of 6-methylene-6-desoxy-N-cyclopropylmethyl-14-hydroxydihydronormorphone over the desired period of time. The matrix may be made, for example, of a mixture of cellulosic polymers such as hydroxypropyl methylcellulose having a molecular weight of from about 20,000 to about 140,000 and which may be advantageously mixed with polyvinylpyrrolidone which has a molecular weight of from about 20,000 to about 100,000, and preferably has a molecular weight of about 40,000. When polyvinylpyrrolidone is used it is preferably used in an amount of about 0.2 to about 0.5 parts per unit weight of cellulosic polymer. The total number of granules is contemplated as being at least about 200 per oral dosage unit form, and up to about 1000, with a typical dosage unit form comprising a total of about 600 granules. The granules may be administered in the form of a solid tablet that is made by compressing the granules together with typical tableting excipients such as from about 0.5 to about 3 percent magnesium stearate, or they may be placed in a capsule. As the capsule form of the oral sustained release dosage unit form, the granules may be directly filled into the capsule where the capsule is designed to be swallowed, as such. Or, in a preferred embodiment of the present invention for either patients in an extremely senile condition or having a difficulty in taking large tablets or capsules, the granules are first coated in an air suspension column (Glatt GmbH, West Germany, 6 inch column) with a polyvinylpyrrolidone film. The capsule serves only to measure the number of granules for the dosage, and the drug is administered by sprinkling the dosage form into the dinner main course or vegetables of the subject being treated to assure both patient compliance and to permit a form that is easier to swallow for an elderly patient.

EXAMPLE I

While sleep disturbances with interruptions in breathing patterns often occur in the elderly with heart or lung illnesses, such disturbances have not been so generally recognized in the apparently "healthy" population of the elderly who were suspected of possible sleep disturbances. A series of several such elderly "healthy" subjects were tested in a specially designed hospital sleep center (Mt. Sinai Medical Center, Miami Beach, Fla.), in a room with a normal hospital bed but where each patient was first wired at several points on the head and chest. Brain waves were measured through the terminals glued to various points on the head, and chest movements measured breathing patterns. Calibration of chest movements to breathing was determined through individual experiments on each patient where a specified amount of air was exhaled into a specially designed apparatus for this purpose, and the amount of air and the chest movements were calibrated. Each patient was permitted to sleep in the darkened hospital room, with a window for observation by a technician for the purpose of general monitoring and to observe the need, if any, for the reattachment any of the terminals that become disconnected during extreme sleep movements.

The patients were observed to have patterns of breathing with periodic total cessation of breathing for periods generally of 15 to 30 seconds. These periods of total sleep interruption took place repeatedly, generally with at least about 200 such episodes per evening. Brain wave disturbances indicated disruption of proper sleep patterns. The cessations of breathing coupled with the disruptions of "normal" sleep cause an effective sleep deprivation in the patients which results in the appearance of senility during waking hours, i.e., the effectively sleep-deprived patients acts confused due to the failure to receive adequate effective rest during the regular period for sleep. The very small amount of oxygen deprivation, while not important medically when measured on an individual night's loss of sleep, cumulatively is believed to be a contributing factor to senility problems in the elderly in situations where the observation of senility over a prolonged period of time shows the very gradual onset of this condition.

EXAMPLE II

An experiment was conducted to determine the effect of an endorphin blocker to block the appearance of breathing lapses as described in Example I. The experimental model takes into consideration the observation that the localization of opiate receptors in the brain stem and the observed inverse relationship between $PaO_2$ and plasma endorphin activity (J. Clin. Endo. 79:888, 1979) indicates that endorphins may be involved in the regulation of breathing during hypoxemia. Breathing patterns during mild hypoxemia in the wakeful state were measured and assessed the effects of 1-N-allyl-14-hydroxynordihydromorphinone were assessed under these conditions. In a randomized double blind design, six normals received intravenous 1-N-allyl-14-hydroxynordihydromorphinone (2 mg) or placebo (saline) on two days. Breathing patterns monitored by non-invasive respiratory inductive plethysmography and transcutaneous oxygen tension ($TcPO_2$) were measured continuously at baseline (BL) and after breathing 100% nitrogen via the nasal cannula at two, four, six, and eight L/min and air-sham at 6 L/min for 10 minutes each. In a related study, TcpO$_2$ (mmHg) of 66 ($\pm$6) and 37 ($\pm$5) corresponded to a SaO$_2$ of 97 and 88%, respectively by ear oximetry. Results were (mean$\pm$SD):

|  |  | 100% N$_2$ (L/min) |  |  |  | Airsham |  |
|---|---|---|---|---|---|---|---|
|  | BL | 2 | 4 | 6 | 8 | 6 L/min | recovery |
| TcPO$_2$ (Placebo) | 68 $\pm$ 10 | 63 $\pm$ 8 | 52 $\pm$ 7 | 44 $\pm$ 6 | 40 $\pm$ 7 | 73 $\pm$ 14 | 82 $\pm$ 12 |
| (Naloxone) | 67 $\pm$ 7 | 63 $\pm$ 10 | 55 $\pm$ 11 | 45 $\pm$ 11 | 35 $\pm$ 11 | 70 $\pm$ 11 | 76 $\pm$ 15 |

After administration of placebo, irregular breathing with fluctuations in tidal volume (V$_T$) developed in all subjects at N$_2$ 2 L/min. As the TcPO$_2$ decreased, irregularity of V$_T$ increased and at N$_2$ 8 L/min, Cheyne-Stokes Respiration (SCR) developed in all subjects. After administration of Naloxone, no irregularity of breathing was seen at N$_2$ 2 and 4 L/min: as the TcPO$_2$ decreased, an irregular breathing developed in all subjects but SCR occurred in only 3 of 6 subjects at N$_2$ 8 L/min. On both days, as the TcPO$_2$ decreased, V$_T$, minute ventilation, fractional inspiratory time, and mean inspiratory flow increased in a linear fashion followed by a plateau whereas frequency and inspiratory time decreased linearly. Thus, mild hypoxemia produces irregular tidal breathing and Cheyne-Stokes Respiration in awake normals. This effect is considered to be related to endorphin release since it is blunted by the administration of 1-N-allyl-14-hydroxynordihydromorphinone.

EXAMPLE III

To retard the onset of breathing interruptions of the type described in Example I, a patient, prior to retiring, is given a tablet containing 50 mg 6-methylene-6-desoxy-N-cyclopropylmethyl-14-hydroxydihydronormorphone in the form of its hydrochloride, for the purpose of obviating the periodic sleep interruptions discussed in Example I.

EXAMPLE IV

There are blended 60 gm 6-methylene-6-desoxy-N-cyclopropylmethyl-14-hydroxydihydronormorphone hydrochloride, 120 gm polyvinylpyrrolidone (mw 40,000), and 240 gm hydroxypropylmethylcellulose (mw=120,000, Methocel, K15M, Dow Chemical) and the resulting blend is granulated with 150 ml deionized water. Granules are produced from this mixture and, after drying at a temperature of 50° C., grinding takes place to produce the granules.

EXAMPLE V

Granules produced in accordance with Example IV are passed through a 14 mesh screen and are then lubricated with 5 mg magnesium stearate to produce tablets having a total weight of about 500 mg which are compressed from this mixture.

EXAMPLE VI

Granules produced in accordance with Example IV are passed through a 14 mesh screen, and a total weight of 500 mg of such granules are placed in a capsule which cannot be readily pried open but which dissolves in the gastrointestinal tract upon ingestion.

EXAMPLE VI

Granules produced in accordance with Example IV are passed through a 14 mesh screen, and thereafter coated in an air suspension column (Glatt, six inch). The granules are coated with a thin layer of polyvinylpyrrolidone (mw=40,000, "Kollidon 30") which has first been mixed in ten parts isopropanol, to provide tasteless, coated granules. After drying, a total weight of 500 mg of such granules is placed in a capsule which is easy to open, and designed for the patient, relative, friend, or hospital worker to open and sprinkle into the dinner meal of the patient to assure patient compliance.

EXAMPLE VII

A normal subject (age 25) is determined to have normal arterial oxygen tension of 95 but a geriatric patient (age 75) is found to have a tension of 75. Decreased oxygen in the bloodstream promotes endorphins, which lead to a variety of aging related problems, including a higher threshold of pain tolerance, constipation, impotence, less responsiveness of the respiratory center in the brain to carbon dioxide in the blood and sleep apneas. Provision of an endorphin blocker, particularly the opioid antagonists, obviates the effects of the lowered oxygen level.

As examples of said endorphin-blocking compound may be mentioned 1-N-allyl-14-hydroxynordihydromorphinone and, as a preferred embodiment for oral administration, 6-methylene-6-desoxy-N-cyclopropylmethyl-14-hydroxydihydronormorphone. Naltrexone is also suitable. A daily dosage of from about 20 to about 100 mg per day is contemplated for 6-methylene-6-desoxy-N-cyclopropylmethyl-14-hydroxydihydronormorphone in the oral dosage unit form, and in a more preferred embodiment, it is specifically contemplated that a sustained release dosage form is provided to give at least about six to about eight hours release of 6-methylene-6-desoxy-N-cyclopropylmethyl-14-hydroxydihydronormorphone. With such an oral sustained release dosage unit form, the subject typically takes a single tablet, capsule, or granules just after dinner, so that the medication will be provided in the bloodstream throughout the period of overnight sleep.

What is claimed is:

1. A method of permitting restful sleep at high altitudes comprising administering to a patient susceptible to Cheyne-Stokes respiration at said high altitudes a pharmaceutically acceptable amount of 6-methylene-6-desoxy-N-cyclopropylmethyl-14-hydroxydihydronormorphone which is capable of blocking the action of endogenous endorphins, whereby sleep interruptions characteristic of Cheyne-Stokes respiration are alleviated.

2. The method of claim 1 wherein 6-methylene-6-desoxy-N-cyclopropylmethyl-14-hydroxydihydronormorphone is in the form of its hydrochloride.

3. A method of retarding the advance of senility in a patient having an erosion of viable brain cells due to the periodic disruption of a necessary minimum oxygen level to sustain healthy brain tissue, said periodic cessation of breathing which causes sufficient total oxygen deprivation over a prolonged period of time to adversely affect the health of the brain cells, said method comprising administering to said patient 6-methylene-6desoxy-N-cyclopropylmethyl-14-hydroxydihydronormorphone in an amount sufficient to alleviate said periodic cessation of breathing, whereby said necessary minimum oxygen level to sustain healthy brain tissue is maintained during periods of sleep.

4. The method of claim 3 wherein said 6-methylene-6-desoxy-N-cyclopropylmethyl-14-hydroxydihydronormorphone is administered as an oral dosage unit form.

5. The method of claim 4 wherein said oral dosage unit form is a sustained release vehicle that is capable of providing said chemical agent during an entire period of overnight sleep.

* * * * *